(12) United States Patent
Torres et al.

(10) Patent No.: US 11,573,179 B2
(45) Date of Patent: Feb. 7, 2023

(54) TISSUE PROCESSING

(71) Applicant: APPLIKATE TECHNOLOGIES LLC, Washington, DC (US)

(72) Inventors: Richard Torres, East Haven, CT (US); Michael Levene, Washington, DC (US)

(73) Assignee: APPLIKATE TECHNOLOGIES LLC, Washington, DC (US)

( * ) Notice: Subject to any disclaimer, the term of this patent is extended or adjusted under 35 U.S.C. 154(b) by 0 days.

(21) Appl. No.: 17/000,994

(22) Filed: Aug. 24, 2020

(65) Prior Publication Data

US 2021/0072156 A1 Mar. 11, 2021

Related U.S. Application Data

(60) Provisional application No. 62/890,246, filed on Aug. 22, 2019.

(51) Int. Cl.
| | |
|---|---|
| *G01N 1/30* | (2006.01) |
| *G01N 21/64* | (2006.01) |
| *G01N 33/483* | (2006.01) |

(52) U.S. Cl.
CPC ........... *G01N 21/6428* (2013.01); *G01N 1/30* (2013.01); *G01N 21/6458* (2013.01); *G01N 33/4833* (2013.01); *G01N 2001/302* (2013.01)

(58) Field of Classification Search
None
See application file for complete search history.

(56) References Cited

U.S. PATENT DOCUMENTS

| | | | | |
|---|---|---|---|---|
| 6,090,618 A | * | 7/2000 | Parmacek | A61P 9/10 435/320.1 |
| 6,183,784 B1 | * | 2/2001 | Read | A61P 1/00 424/535 |
| 6,232,092 B1 | * | 5/2001 | Rogers | G01N 1/30 435/40.5 |
| 2007/0134154 A1 | * | 6/2007 | Chang | A61K 9/1272 424/1.49 |
| 2008/0015448 A1 | * | 1/2008 | Keely | A61B 6/502 600/477 |
| 2009/0246824 A1 | * | 10/2009 | Wiederhold | G01N 1/286 435/40.52 |
| 2010/0261958 A1 | * | 10/2010 | Webb | G02B 13/146 600/162 |
| 2012/0112098 A1 | * | 5/2012 | Hoyt | G01N 21/6458 250/459.1 |
| 2016/0003715 A1 | * | 1/2016 | Torres | G01N 33/4833 435/40.52 |

* cited by examiner

*Primary Examiner* — Neil N Turk
(74) *Attorney, Agent, or Firm* — Brown Rudnick LLP; Thomas C. Meyers

(57) ABSTRACT

The present invention relates to systems and methods for tissue processing and imaging including a counterintuitive inverse relationship between protein dye concentration and tissue sample protein content. Varying dye concentration in such a manner affords higher quality fluorescent imaging at depth in tissue when using optical sectioning microscopy or second harmonic generation (SHG) analysis. Methods of the invention thereby provide more usable histopathology images while reducing waste and reagent costs and are of particular utility in combination assays that include simultaneous protein and nuclear staining and SHG analysis.

14 Claims, 2 Drawing Sheets

TISSUE PROCESSING

RELATED APPLICATIONS

This application claims priority to and the benefit of U.S. Provisional Application No. 62/890,246, filed on Aug. 22, 2019, the content of which is hereby incorporated by reference in its entirety.

FIELD OF THE INVENTION

The present disclosure relates to tissue processing and imaging systems and methods.

BACKGROUND

Histology and histopathology involve the study of cells and tissues under a microscope to diagnose and monitor diseases, such as cancer. Differentially staining and imaging various structures in tissue can provide detailed information at the cellular and sub-cellular level that is indispensable in tissue analysis including diagnostic and prognostic evaluation.

While much of the field still depends on visual examination by trained medical professionals, the development of new processing and imaging techniques has increased throughput and imaging quality on the front end. For example, treatment with fluorescent dyes and the use of confocal microscopy and multiphoton microscopy provide high-quality images with good cellular detail at various depths in tissue. The ability to stain and image structures at depth in tissue allows for three-dimensional analysis of tissue samples which improves diagnostic accuracy. Additionally, short-pulse, high-intensity laser light can be used to generate mapping of second-harmonic generation (SHG), which is useful in imaging protein structures such as collagen and amyloid. Collagen imaging in liver can be used to quantify fibrosis, a marker of liver injury in a variety of hepatic conditions and an important clinical prognostic factor.

While these techniques represent significant advancement in the field of histology and histopathology, scaling up their use for every-day clinical application requires streamlining the processes to reduce costs, increase throughput, and provide consistent results. Many of the dyes used can be expensive and represent a significant portion of the reagent cost in the above techniques. Furthermore, dye concentrations are not standardized and providing consistent quality when imaging at depth can be problematic.

SUMMARY

The present invention provides tissue processing techniques using tissue-specific fluorescent dye concentrations for achieving increased image quality and contrast at depth along with reduced waste as compared to existing techniques. Systems and methods of the invention recognize that imaging quality at depth is dependent on tissue type and associated protein content. Despite a logical assumption that imaging of samples with higher protein content would benefit from higher fluorescent protein dye concentration, the inventive methods observe that image quality for such samples actually benefits from lower concentration of fluorescent protein dye during specimen preparation.

Practically applying those principles, methods of the invention include assessing tissue samples for protein content and varying the protein dye concentration used in staining based on that protein content. The tissue-specific protein dye concentrations are generally higher for tissues having lower protein content (e.g., renal tissue) than in tissues with higher protein content (e.g., epithelial tissue). Relatively higher concentrations result in improved contrast at depth in samples with relatively low protein content. However, similar concentrations of protein dyes in samples with higher protein content result in increased signal absorption from deeper levels of the sample, decreasing contrast and degrading image quality in optical sectioning microscopy methods (e.g., confocal imaging, multiphoton imaging, and selective plane illumination). Increased absorption can affect both nuclear and protein fluorescent signals based on the relative emission and absorption spectra of the specific dyes employed. However, due to the overall higher concentration of protein than nucleic acids in tissue, the interplay between protein-sensitive dye concentration and protein content has a significantly greater impact on image quality at depth.

An additional benefit of tailoring the dye concentration to the protein content is the efficient use of expensive reagents. Counterintuitively using less dye to stain tissue with higher protein content results in cost savings that can help promote the fluorescent imaging techniques described above for every-day clinical use.

The increased signal absorption resulting from excessive dye concentration in protein-rich samples can also affect the ability to detect second harmonic generation at depth. As noted above, SHG detection is highly relevant for fibrosis detection in kidney and liver samples. Accordingly, tailoring dye concentration to the protein content of a sample also supports more accurate SHG detection and the related diagnostic and prognostic evaluations afforded by SHG detection in certain tissues.

Methods for deep imaging of thick tissue samples with combined nucleic acid and protein-specific dyes have been disclosed in U.S. patent application Ser. Nos. 14/324,019 and 14/790,917, the contents of each of which are incorporated herein by reference. Combined protein and nucleic acid staining can be used to accurately reproduce common histologic stains for pathologist interpretation such as the Hematoxylin and Eosin stain (H&E) and the so-called Trichrome stain. In such applications, with the benefit of normalization of fluorescent signal intensity after signal acquisition and the adaptive nature of back-end visual analysis, the use of the lower concentrations of protein-specific fluorescent dyes in high protein density samples still yields images of sufficient quality to replicate standard H&E and Trichrome staining.

Aspects of the invention include a method of imaging a tissue sample by determining a protein dye concentration for a given tissue type based on the protein density or content of that tissue type. The protein dye concentration is inversely related to the protein density. A tissue sample of the tissue type is then contacted with a solution comprising at least one fluorescent protein dye at the determined concentration for that tissue type. A tissue sample image can then be produced by measuring intensity values of fluorescence of the tissue sample at a depth greater than about 200 μm. The solution may include a fluorescent nuclear dye which may be selected from DAPI, SYTOX dyes, SYTO dyes, propidium iodide, acridine orange, or Hoechst dyes.

The at least one fluorescent protein dye may include eosin, Rhodamine B (RhB), or ANS. Producing the tissue sample image can include second harmonic generation (SHG). In certain embodiments, the tissue sample may include collagen. The tissue sample can be a liver sample and the at least one fluorescent protein dye may include eosin at about 0.02% of alcoholic stock solution. typical example of alcoholic stock solution of eosin is Eosin Y, 1% alcoholic solution, non-acidic (Polysciences, Inc, Warrington Pa.).

In various embodiments, the tissue sample may be renal tissue and the at least one fluorescent protein dye can include eosin at about 0.4% of alcoholic stock solution. Alternatively, the tissue sample can be epithelial tissue and the at least one fluorescent protein dye may include eosin at about 0.04% of alcoholic stock solution. The sample image can be a three dimensional (3-D) sample image. The tissue sample image can be produced using an optical sectioning microscope. The optical sectioning microscope may be a multiphoton microscope (MPM), a confocal microscope, a structured illumination microscope, a super-resolution microscope, a selective plane illumination microscope (SPIM), a side-plane illumination microscope, a spinning disk confocal microscope, or a deconvolution microscope.

The solution may further comprise a fixative such as methacarn. Methods of the invention may include contacting the tissue sample with a clearing solution before producing the tissue sample image. The clearing solution may include benzyl alcohol and benzyl benzoate. The solution can include a permeation enhancer. In certain embodiments methods of the invention may include converting the intensity values to effective optical densities, such that the optical densities recreate the coloration of a stain in the tissue sample image.

DETAILED DESCRIPTION

Figures 1, 2, 3, 4:
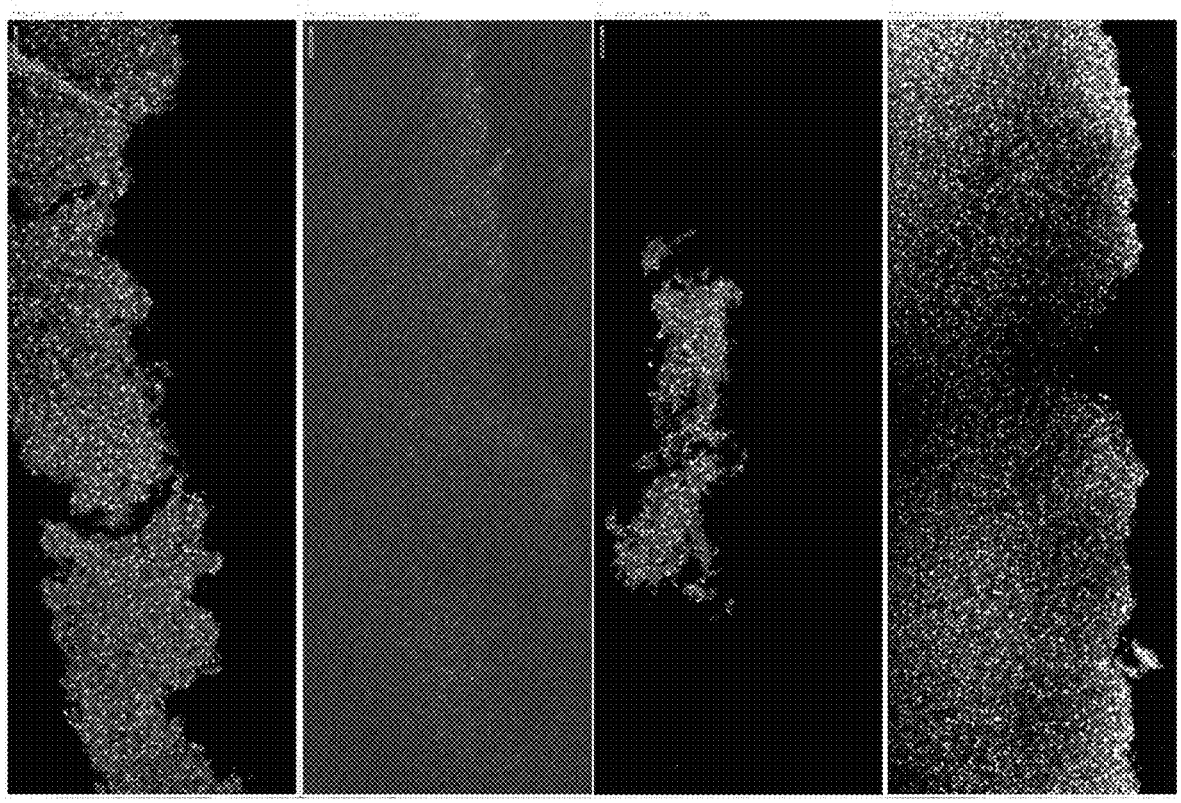
FIG. 1 shows an image of an eosin-stained liver sample at 50 μm of depth where a dye concentration of 2% of alcoholic stock was used in staining.
FIG. 2 shows an image of an eosin-stained liver sample at 500 μm of depth where a dye concentration of 2% of alcoholic stock was used in staining.
FIG. 3 shows an image of an eosin-stained liver sample at 50 μm of depth where a dye concentration of 0.02% of alcoholic stock was used in staining.
FIG. 4 shows an image of an eosin-stained liver sample at 500 μm of depth where a dye concentration of 0.02% of alcoholic stock was used in staining.

The present invention provides systems and methods for processing tissue samples for imaging and visual histologic analysis at depth. Methods of the invention recognize an inverse relationship between protein content in a tissue sample and the protein dye concentration required to provide suitable images at depth.

As described in U.S. patent application Ser. Nos. 14/324,019 and 14/790,917 and discussed in more detail below, methods for deep imaging of tissue samples simultaneously stained with both nucleic acid-specific and protein-specific dyes have been previously reported. Such techniques have been applied to reproduce common histologic stains for pathologist interpretation such as H&E and Trichrome stains. The present disclosure operates on the previously unknown principle that imaging quality at depth is dependent on tissue type where, counterintuitively, imaging of samples with higher protein content benefits from lower concentration of fluorescent protein dye during specimen preparation. Meanwhile, samples with relatively low protein content exhibit improved contrast at depth when stained with high concentrations of fluorescent protein dyes.

High concentrations of protein dyes in protein dense tissues were shown to result in markedly increased absorption of fluorescent signal from deeper levels, thereby decreasing contrast and degrading image quality. That phenomenon can be observed when using any method of optical sectioning microscopy such as confocal imaging, multiphoton imaging, and selective plane illumination and supports the counterintuitive inverse relationship underpinning certain methods of the invention.

Depending on the relative emission and absorption spectra of the dyes employed, the increased absorption described above can affect both nuclear and protein-specific fluorescent dye signals. However, the relative concentration of protein in tissue is much higher than nucleic acids and, accordingly, protein content and protein-specific dye concentration are the significant drivers in signal weakening in a combined protein and nucleic acid staining assay. The inverse dye concentration to protein content methods described herein can be applied to both single-stain assays as well as combined protein and nucleic acid stain assays. Inversely varying protein-specific stain concentration based on sample protein content benefits contrast and signal intensity not only in protein dye imaging but also in imaging of nuclear dyes in the aforementioned combined stain assays.

Using a fluorescent protein dye concentration inversely related to protein density of the tissue sample also provides the benefit of reducing waste and, therefore reagent costs by conserving dye when applied to imaging at any depth. However, the signal weakening at depth associated with saturation from a too-high dye to protein content ratio can be observed when imaging beyond about 200 μm in protein-rich tissue. Accordingly, additional image quality benefits can be observed in optical sectioning microscopy techniques that rely on imaging at such depths.

Figure 5:
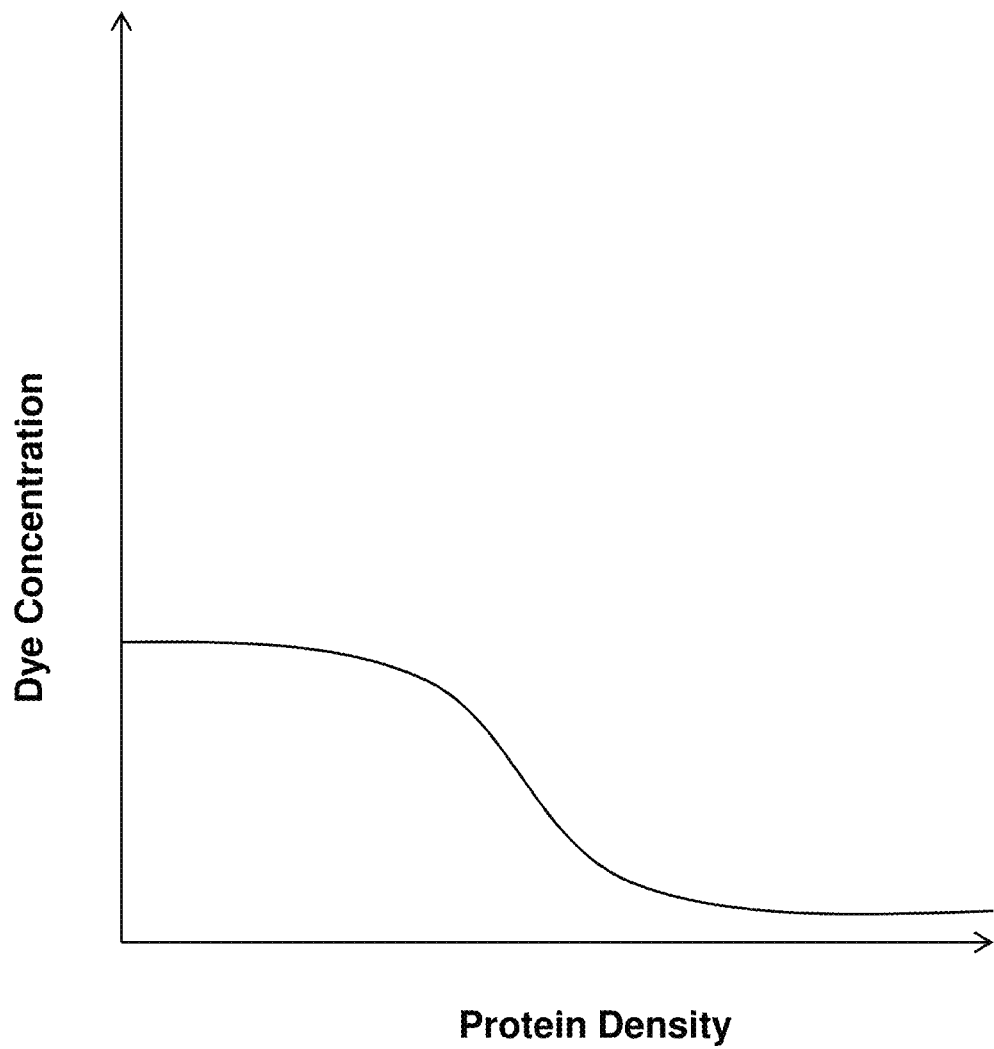
FIG. 5 shows an exemplary curve showing an inverse relationship between tissue protein content and fluorescent protein dye used in staining the tissue.

An exemplary graph showing an inverse relationship between tissue protein density and dye concentration is provided in FIG. 5. As illustrated, there is a minimum and maximum level of dye concentration that can be applied regardless of protein concentration. At very low concentrations of protein there is a threshold level of dye concentration above which the protein is saturated and any additional stain is wasted. At very high protein densities, there is a minimum threshold of dye concentration required to achieve any dye penetration and fluorescent signal. As represented in FIG. 5, it is in the middle range of tissue protein densities where variations in dye concentration inverse to protein density yield maximum benefit.

Methods of processing and imaging tissue samples according to the invention can be applied to any type of sample including a cell or group of cells, an organism, a tissue, cell lysates, a cell culture medium, or a bioreactor sample. In preferred embodiments, the sample is a tissue sample with a thickness sufficient to allow for the imaging depths described herein. Examples of tissues contemplated for application of the described methods include skin, muscle, bowel, breast, heart, kidney, lung, liver, skin, placenta, prostate, pancreas, uterus, bone, bone marrow, brain, stomach, muscle, cartilage, lymph node, adipose tissue, tonsil, gall bladder, and spleen.

As detailed below, methods of the invention are particularly applicable when processing and imaging tissue samples with relatively high (e.g., epithelial tissue) or low (e.g., renal tissue) protein content or in tissue where fibrosis is a diagnostic indicator (e.g., kidney or liver tissue). The table below notes examples of tissues and average protein content.

| Tissue | Approximate % by mass protein |
| --- | --- |
| Adipose | 4 |
| Connective Tissue | 37 |
| Brain Tissue | 10 |
| Heart Tissue | 17 |
| Lung | 17 |
| Liver | 18 |
| Kidney | 18 |
| Skeletal Muscle | 20 |
| Pancreatic Tissue | 13 |
| Cartilage | 11 |
| Yellow Marrow | 4 |
| Red Marrow | 20 |
| Bone Tissue | 22 |
| Skin | 25 |
| Ovary Tissue | 14 |
| Thyroid Tissue | 14 |

While overall protein content can help inform decisions on dye concentration, protein density is of primary importance. For example, as noted in the examples, kidney tissue is composed of tubular structures and is highly vascularized leading to a lower protein density than might be indicated by its level of overall protein content. As discussed below, deep tissue imaging of kidney tissue accordingly tolerates a higher dye concentration than a protein-dense tissue such as epithelium.

Tissue samples may be obtained through any method known in the art including surgery, biopsy, fine needle aspiration, culture, or autopsy. Samples may be fresh or fixed. Processing may include fixing the tissue sample before imaging. Fixing may be performed simultaneously with staining by inclusion of one or more dyes in the fixative solution. Fixing and staining can be performed along with a dehydrant and/or a permeation enhancer. In various embodiments, tissue samples can be cleared prior to imaging.

Dehydration facilitates the removal of water from a sample so that clearing agents with low water solubility can subsequently be used. Exemplary dehydrants include alcohols such as methanol, ethanol, and propanol. Methacarn may act as a dehydrant and fixative and dehydration can be performed simultaneously with fixation.

Fixation may be performed using any method known in the art including treatment with aldehydes (e.g., formaldehyde (paraformaldehyde, formalin), glutaraldehyde, acrolein (acrylic aldehyde), glyoxal (ethanedial, diformyl), malonaldehyde (malonic dialdehyde), diacetyl (2,3-butanedione), and polyaldehydes; alcohols (i.e., protein-denaturing agents; e.g., acetic acid, methanol, ethanol), polyvinyl alcohols, heavy metal oxidizing agents (i.e., metallic ions and complexes; e.g., osmium tetroxide, chromic acid); agents of unknown mechanism, such as chloro-s-triazides, cyanuric chloride, carbodiimides, diisocyanates, diimido esters, diethylpyrocarbonate (diethyl oxydiformate, ethoxyformic anhydrate), picric acid, mercuric chloride (corrosive sublimate, bichloride of mercury), and other salts of mercury, and acetone. Furthermore, any combination of fixative agents can be used including Carnoy's fixatives, methacarn, Wolman's solution, Rossman's fluid, Gendre's fluid, Bouin's fluid, Zenker's fluid, Helly's fluid, B5 fixative, Susa fluid, Elftman's fixative, Swank and Davenport's fixative, Lillie's alcoholic lead nitrate, and cetylpyridinium chloride (C.P.C.). Additives can be used including tannic acid, phenol, transition metal salts (zinc), lanthanum, lithium, potassium.

As noted, at least one fluorescent dye may be added to the sample during tissue processing independent of or in coordination with other processing steps. Examples of fluorescent dyes include POPO-1, TOTO-3, TAMRA, BOXTO, BEBO, SYBR DX, SYTOX dyes, SYTO dyes, Alexa dyes, fluorescein, rhodamine, propidium idodide, Hoechst dyes, tetramethylrhodamine, R-phycoerythrin, Cy-3, Cy-5, Cy-7, Texas Red, Phar-Red, allophycocyanin (APC), fluorescein amine, eosin, dansyl, umbelliferone, 5-carboxyfluorescein (FAM), 2'7'-dimethoxy-4'5'-dichloro-6-carboxyfluorescein (JOE), 6 carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), 5-(2'-aminoethyl)aminonaphthalene-1-sulfonic acid (EDANS), 8-Anilino-1-naphthalenesulfonic acid ammonium salt (ANS), 4-acetamido-4'-isothiocyanatostilbene-2,2' disulfonic acid, acridine, acridine isothiocyanate, acridine orange (N,N,N',N'-tetramethylacridine-3,6-diamine), R-amino-N-(3-vinylsulfonyl)phenylnaphthalimide-3,5, disulfonate (Lucifer Yellow VS), N-(4-anilino-1-naphthyl)maleimide, anthranilamide, Brilliant Yellow, coumarin, 7-amino-4-methylcoumarin, 7-amino-4-trifluoromethylcouluarin (Coumarin 151), cyanosine, 2-(4-amidinophenyl)-1H-indole-6-carboxamidine (DAPI), 5',5"-dibromopyrogallol-sulfonephthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 4-dimethylaminophenylazophenyl-4'-isothiocyanate (DABITC), eosin isothiocyanate, erythrosin B, erythrosin isothiocyanate, ethidium, 5-(4,6-dichlorotriazin-2-yl)aminofluorescein (DTAF), QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron® Brilliant Red 3B-A), lissamine rhodamine B sulfonyl chloride, rhodamine B, rhodamine 123, rhodamine X, sulforhodamine B, sulforhodamine 101, sulfonyl chloride derivative of sulforhodamine 101, tetramethyl rhodamine, thiazole orange, riboflavin, rosolic acid, and terbium chelate derivatives.

The at least one fluorescent dye may be a nuclear dye or a protein dye as methods of the invention benefit deep imaging quality of either and especially combined assays. Examples of nuclear dyes include DAPI, SYTOX dyes, SYTO dyes, propidium iodide, acridine orange, and Hoechst dyes. Examples of protein dyes include eosin, Rhodamine B (RhB), and ANS. A morphology preservative may be added to the sample during processing to maintain the nuclear structure of the cells and reduce shrinking or swelling during processing. Morphology preservatives include acetic acid, trichloroacetic acid, formaldehyde, dioxane, and chloroform.

Permeation enhancers are thought to accelerate the penetration of fixative, dehydrant, dyes, and clearing agents during processing. Examples of permeation enhancers include acids such as acetic acid, methacarn comprising acetic acid, sulphoxides such as dimethylsulfoxide (DMSO), azone, pyrrolidones, propylene glycol, fatty acids, essential oils, phospholipids, s-collidine, and surfactants such as Tween.

In processing methods including fixation, the fixation step may be performed under any condition that promotes rapid tissue processing, such as an elevated temperature ranging from about 20° C. to about 75° C. A fixation step can be performed for any suitable length of time. In the interest of rapid throughput for clinical applications, the fixation step (including simultaneous staining and/or dehydration) may be performed over a period of time about 1 hour.

In various embodiments, tissue sample processing includes clearing the sample to provide increased depth and clarity in sample images. Clearing can be performed through contacting the sample with a clearing solution. Clearing involves replacing water in the sample with a clearing solution that has a higher refractive index than water that more closely resembles that of proteins and organelles to be imaged such that light scattering is reduced, especially when imaging at depth. Examples of organic solvents useful as clearing agents include, benzyl alcohol, benzyl benzoate, xylene, limonene, benzene, toluene, chloroform, petroleum ether, carbon bisulfide, carbon tetrachloride, dioxane, glycerol, sugar solutions, dibenzyl ether, clove oil, and cedar oil. In preferred embodiments, the clearing agent is benzyl alcohol/benzyl benzoate (BABB).

Tissue sample imaging techniques contemplated in conjunction with the methods of the invention include fluorescence based sectioning imaging methods. Examples of fluorescence based sectioning imaging methods include multiphoton microscopy (MPM), side-plane illumination microscopy, traditional confocal microscopy, spinning disk confocal microscopy, structured illumination microscopy, and the like. Tissue sample images may be produced by measuring intensity values of the fluorescence of the tissue sample, and converting the intensity values to effective optical densities, such that the optical densities recreate the coloration of a stain in a produced image of the tissue sample.

Imaging methods described herein may be used to produce images that mimic traditional pathology stains. Examples of pathology stains which can be reproduced using the methods of the present invention include hematoxylin, eosin, wright, giemsa, Masson's trichrome, Jones, trichrome, periodic acid Schiff (PAS) and reticulin stains. Combinations of pathology stains can also be reproduced using methods of the present invention including hematoxylin and eosin (H&E) or wright and giemsa.

In some embodiments, higher-order harmonic generation may be used alone or in conjunction with the above imaging analysis. Higher-order harmonic generation permits the recreation of additional specialized histological stains, such as collagen stains like trichrome and silver stains like Jones stain. Of particular interest is second harmonic generation (SHG) which results from multiphoton excitation of asymmetric repeating proteins such as collagen, and may be used for simple identification and quantification of collagen fibrosis and amyloid in combination with imaging methods, such as MPM.

EXAMPLES

Exemplary applications of the inventive methods include H&E-like images at depth of kidney and skin, obtained by multiphoton laser excitation after simultaneous fluorescent staining with the protein-specific fluorescent dye eosin and the nucleic acid-specific fluorescent dye DAPI. Although both tissue types might seem superficially to represent similarly dense tissues, they differ significantly in overall protein concentration. Kidneys are composed of tubular structures and are highly vascular, resulting in significantly lower overall protein content than the skin epithelium, which is composed of tightly packed cells with relatively few vessels and usually possess an overlying layer of tightly packed keratin protein without vascularization. Relatively high concentration eosin dye in fluorescent kidney protein staining, such as about 0.4% of alcoholic stock solution, results in a clear visualization of diagnostically relevant structures such as capillary walls of the blood filtering unit called the glomerulus, and images collected over a depth of about 1 mm are essentially unaffected by the protein dye that lies between the excited fluorophore and the fluorescence detectors. The same high concentration of protein fluorescent dyes results in marked dimming of both the eosin and DAPI signals in images beyond about 200 μm deep in relatively protein-rich keratinized epithelial tissue. However, performing the same dyeing procedure as above but with a 10-fold lower concentration of eosin (about 0.04% of alcoholic stock solution) resulted in adequate contrast of protein structures at surface as well as more homogeneously bright and readable staining at depths beyond 300 μm. As such, varying concentrations of the fluorescent dye for protein staining are preferred based on the overall protein content of the specimen.

A second exemplary application is in the three dimensional characterization of collagen in liver. Although liver is not an epithelial tissue, it has a relatively high protein content which is related to its high metabolic activity as a primary detoxifying organ. Collagen has a property that is useful for imaging using multiphoton pulsed laser excitation. If the intensity of light pulses is high enough, such as when a femtosecond pulsed laser is focused by a microscope objective, then the energy of two photons reaching the collagen fiber simultaneously is combined into one photon of twice the energy (half the wavelength). In liver, that second harmonic generation (SHG) signal is derived almost exclusively from collagen and can thus be exploited as a quantifiable measure of fibrosis. Fibrosis is a marker of liver injury in a variety of hepatic conditions and an important clinical prognostic factor. Visualization of collagen throughout a liver specimen is particularly desirable as it represents a more extensive and thereby precise measure of sample collagen. Accordingly, the application of the inventive methods to provide detailed SHG analysis at depth in hepatic tissue has notable diagnostic and prognostic benefits.

Normalization of the refractive index throughout a tissue specimen, such as through clearing, can further improve collagen maps of thick liver and other tissue specimens. SHG analysis can be performed concurrently with protein and nucleic acid imaging, reducing overall work and processing time while maximizing informational content derived with imaging. However, in such combined applications, while using wavelengths between about 750 nm and 900 nm, the SHG signal is severely attenuated at depth if the concentration of eosin, staining the protein, is high. When the SHG signal is collected in transmittance rather than through the excitation lens, the effect is such that surface excitation of SHG at higher protein dye concentrations results in a more attenuated signal. In both scenarios, minimizing eosin concentration during staining to a degree that still allows visualization of microscopic protein-rich structures aids in maximizing the depth at which collagen signal can be simultaneously detected via SHG analysis.

For liver specimens, using staining methods, processing reagents, and multiphoton imaging systems as have been previously described, eosin concentrations around 0.02% of alcoholic stock solutions were found to yield an appropriate balance of protein signal for adequate reproduction of H&E stains while permitting imaging of collagen SHG at several hundred micrometers.

FIGS. 1-4 illustrate such results. Each of FIGS. 1-4 shows an image of a fluorescent signal of a nucleic acid-specific dye applied to a liver sample in combination with a protein-specific dye (eosin) according to methods described above. FIGS. 1 and 3 are at 50 μm of depth with the sample in FIG. 1 being stained with an eosin concentration of 2% of alcoholic stock and the sample in FIG. 3 being stained with an eosin concentration of 0.02% of alcoholic stock. Both images appear of similar quality. However, when the image depth is increased to 500 μm as in FIGS. 2 and 4, the disparity in image quality afforded by the different protein dye concentrations becomes apparent. FIG. 2 shows a liver sample stained with an eosin concentration of 2% of alcoholic stock and FIG. 4 shows a liver sample stained with an eosin concentration of 0.02% of alcoholic stock. The lower eosin concentration used in FIG. 4 provides a much better contrast at 500 μm than the higher concentration used in FIG. 2.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of imaging a tissue sample, the method comprising:
   contacting a tissue sample with a solution comprising at least one fluorescent protein dye to create a stained tissue sample; and
   producing tissue sample images by measuring fluorescence and second harmonic generation of the stained tissue sample, wherein:
   the tissue sample is a liver sample and the at least one fluorescent protein dye comprises eosin at about 0.02% of alcoholic stock solution; or
   the tissue sample is epithelial tissue and the at least one fluorescent protein dye comprises eosin at about 0.04% of alcoholic stock solution.

2. The method of claim 1 further comprising producing the tissue sample images at a tissue depth greater than about 200 μm.

3. The method of claim 1 wherein the solution further comprises a fluorescent nuclear dye.

4. The method of claim 2 wherein the fluorescent nuclear dye is selected from the group consisting of DAPI, SYTOX dyes, SYTO dyes, propidium iodide, acridine orange, and Hoechst dyes.

5. The method of claim 1 wherein the at least one fluorescent protein dye further comprises Rhodamine B (RhB), and ANS.

6. The method of claim 1, wherein producing the tissue sample images comprises producing a three dimensional (3-D) sample image.

7. The method of claim 1, wherein one or more of the tissue sample images is produced using an optical sectioning microscope.

8. The method of claim 7, wherein the optical sectioning microscope is selected from the group consisting of: a multiphoton microscope (MPM), a confocal microscope, a structured illumination microscope, a super-resolution microscope, a selective plane illumination microscope (SPIM), a side-plane illumination microscope, a spinning disk confocal microscope, and a deconvolution microscope.

9. The method of claim 1 wherein the solution further comprises a fixative.

10. The method of claim 1 wherein the fixative is methacarn.

11. The method of claim 1 further comprising contacting the tissue sample with a clearing solution before producing the tissue sample images.

12. The method of claim 1 wherein the clearing solution comprises benzyl alcohol and benzyl benzoate.

13. The method of claim 1 wherein the solution further comprises a permeation enhancer.

14. The method of claim 1 further comprising converting intensity values from the tissue sample images to effective optical densities, such that the optical densities recreate coloration of a stain in one or more of the tissue sample images.

* * * * *